United States Patent
Lorberbaum et al.

(10) Patent No.: US 12,102,347 B2
(45) Date of Patent: Oct. 1, 2024

(54) HOLDER FOR MOUNTING A HANDHELD TOOL TO A SURFACE

(71) Applicant: BING INNOVATIONS, L.L.C.

(72) Inventors: Mark Lorberbaum, Boca Raton, FL (US); Paul Dicesare, Shelton, CT (US); Richard Lawson, Shelton, CT (US); Danial Ferreira, Shelton, CT (US)

(73) Assignee: Bing Innovations, L.L.C., Boca Raton, FL (US)

( * ) Notice: Subject to any disclaimer, the term of this patent is extended or adjusted under 35 U.S.C. 154(b) by 1039 days.

(21) Appl. No.: 16/965,035

(22) PCT Filed: Jan. 28, 2019

(86) PCT No.: PCT/US2019/015360
§ 371 (c)(1),
(2) Date: Jul. 27, 2020

(87) PCT Pub. No.: WO2019/148073
PCT Pub. Date: Aug. 1, 2019

(65) Prior Publication Data
US 2021/0106349 A1     Apr. 15, 2021

Related U.S. Application Data

(60) Provisional application No. 62/622,367, filed on Jan. 26, 2018.

(51) Int. Cl.
*A47K 10/18*     (2006.01)
*A61B 17/30*    (2006.01)
*A61B 17/00*    (2006.01)

(52) U.S. Cl.
CPC ...... *A61B 17/30* (2013.01); *A61B 2017/0073* (2013.01); *A61B 2017/00862* (2013.01); *A61B 2017/308* (2013.01)

(58) Field of Classification Search
CPC ............ A61B 17/30; A61B 2017/0073; A61B 2017/00862; A61B 2017/308;
(Continued)

(56) References Cited

U.S. PATENT DOCUMENTS

| | | |
|---|---|---|
| 1,485,963 A | 3/1924 | Curry |
| 2,247,258 A | 6/1941 | Shepard |

(Continued)

FOREIGN PATENT DOCUMENTS

| | | |
|---|---|---|
| AU | 2010229783 | 9/2015 |
| CA | 2756890 | 9/2010 |

(Continued)

OTHER PUBLICATIONS

International Preliminary Report on Patentability published Mar. 12, 2014 for PCT/US2012/053744.

(Continued)

*Primary Examiner* — Nkeisha Smith
(74) *Attorney, Agent, or Firm* — Paul D. Bianco; Gary S. Winer; Fleit Intellectual Property Law (57) ABSTRACT

A holder for mounting a hand tool to a surface has a suction cup positionable upon a surface. A yoke is connected to a central area of the suction cup, and is movable in a vertical direction relative to the surface, to distort the suction cup to secure the suction cup and yoke to the surface. A frame includes a cradle shaped to receive and support the hand tool, and a base. An extension connects the base and the cradle. A cam pin is movable within the frame, and has a cam profile that slides along the cam engagement surface of the yoke to displace the yoke along a vertical axis to increase or decrease the pressure between the suction cup and the surface.

17 Claims, 6 Drawing Sheets

(58) Field of Classification Search
CPC ........ F16B 47/006; F16B 47/00; A45D 42/14;
A45D 20/12; A45D 2020/126; A47K
10/18; A47K 19/00; A47K 5/02; A47B
96/02; A47B 96/061; B60R 2011/0056;
B60R 2011/0026
USPC ...................................................... 248/633
See application file for complete search history.

(56) References Cited

U.S. PATENT DOCUMENTS

| | | | |
|---|---|---|---|
| 2,258,857 A | 10/1941 | McCann | |
| 2,574,945 A | 11/1951 | Werner | |
| 3,590,232 A | 6/1971 | Sadowski | |
| 3,620,209 A | 11/1971 | Kravitz | |
| 3,837,595 A | 9/1974 | Boone | |
| 4,091,805 A | 5/1978 | Clark | |
| 4,572,180 A | 2/1986 | Deenadayalu | |
| 4,593,973 A | 6/1986 | Yoshida | |
| 4,785,796 A | 11/1988 | Mattson | |
| 4,867,141 A | 9/1989 | Nakada et al. | |
| 5,437,606 A | 8/1995 | Tsukamoto | |
| 5,542,845 A | 8/1996 | Jenkins | |
| 5,611,771 A | 3/1997 | Taylor | |
| 5,636,988 A | 6/1997 | Murayama | |
| 5,639,238 A | 6/1997 | Fishburne, Jr. | |
| 5,647,851 A | 7/1997 | Pokras | |
| 5,647,853 A | 7/1997 | Feldmann et al. | |
| 5,692,900 A | 12/1997 | Fischer | |
| 5,704,902 A | 1/1998 | Vandenbelt et al. | |
| 5,928,170 A | 7/1999 | Garrigan | |
| 5,938,435 A | 8/1999 | Raspino | |
| 5,989,022 A | 11/1999 | Yamamoto | |
| 6,030,210 A | 2/2000 | Bianchetti | |
| 6,355,007 B1 | 3/2002 | Zuckerbrod | |
| 6,436,035 B1 | 8/2002 | Toth et al. | |
| 6,502,794 B1* | 1/2003 | Ting | F16B 47/00 |
| | | | 248/205.5 |
| 6,602,229 B2 | 8/2003 | Coss | |
| 6,923,762 B1 | 8/2005 | Creaghan, Jr. | |
| 7,244,266 B2 | 7/2007 | Garthe | |
| 7,527,231 B2* | 5/2009 | Zhadanov | F16B 47/00 |
| | | | 248/251 |
| 7,815,155 B2* | 10/2010 | Hung | F16B 47/00 |
| | | | 248/205.5 |
| 7,981,071 B2 | 7/2011 | Goldberg | |
| 8,121,696 B2 | 2/2012 | Vallero | |
| 8,622,952 B2 | 1/2014 | Goldberg | |
| 8,668,664 B2 | 3/2014 | Goldberg | |
| 8,690,872 B2 | 4/2014 | Jayaraj | |
| 8,777,897 B2 | 7/2014 | Butterfield | |
| 8,940,008 B2* | 1/2015 | Kunis | A61M 25/0082 |
| | | | 606/185 |
| 9,168,340 B2 | 10/2015 | Goldberg et al. | |
| 9,200,667 B1* | 12/2015 | Hsu | F16M 13/02 |
| 9,463,287 B1 | 10/2016 | Lorberbaum et al. | |
| 9,539,171 B2 | 1/2017 | Goldberg et al. | |
| 9,675,766 B2 | 6/2017 | Goldberg | |
| 9,732,785 B2* | 8/2017 | Kobayashi | F16B 47/00 |
| 10,363,380 B2* | 7/2019 | Taylor | A61B 17/34 |
| 10,695,508 B2* | 6/2020 | Lorberbaum | A61M 5/422 |
| 2002/0082564 A1 | 6/2002 | Pham | |
| 2003/0040714 A1 | 2/2003 | Coss | |
| 2003/0195644 A1 | 10/2003 | Borders et al. | |
| 2003/0225429 A1 | 12/2003 | Garthe et al. | |
| 2004/0077977 A1 | 4/2004 | Ella | |
| 2004/0254599 A1 | 12/2004 | Lipoma et al. | |
| 2005/0215952 A1 | 9/2005 | Brunel | |
| 2006/0106363 A1 | 5/2006 | Aravena et al. | |
| 2007/0088245 A1 | 4/2007 | Babaev et al. | |
| 2007/0145155 A1 | 6/2007 | Scarlatella | |
| 2007/0150004 A1 | 6/2007 | Colloca et al. | |
| 2007/0156179 A1 | 7/2007 | Karashurov | |
| 2007/0167943 A1 | 7/2007 | Janssen et al. | |
| 2008/0017764 A1 | 1/2008 | Nan | |
| 2008/0086159 A1 | 4/2008 | Zweifler | |
| 2008/0215039 A1 | 4/2008 | Slatkine | |
| 2008/0195006 A1 | 8/2008 | Stark et al. | |
| 2008/0255483 A1 | 10/2008 | Goldberg | |
| 2009/0047624 A1 | 2/2009 | Tsai | |
| 2009/0108153 A1* | 4/2009 | Hung | F16B 47/00 |
| | | | 248/205.8 |
| 2009/0281464 A1 | 11/2009 | Cioanta et al. | |
| 2010/0125172 A1 | 5/2010 | Jayaraj | |
| 2010/0179457 A1 | 7/2010 | Blaine et al. | |
| 2011/0054386 A1 | 3/2011 | Blaine et al. | |
| 2011/0101182 A1* | 5/2011 | Greenspon | E03C 1/066 |
| | | | 248/206.1 |
| 2011/0226922 A1* | 9/2011 | Ishizaki | F16B 47/006 |
| | | | 248/363 |
| 2011/0226924 A1* | 9/2011 | Lin | F16M 11/2014 |
| | | | 248/397 |
| 2011/0270154 A1 | 11/2011 | Goldberg | |
| 2011/0319812 A1 | 12/2011 | Goldberg | |
| 2012/0016292 A1 | 1/2012 | Goldberg | |
| 2012/0029422 A1 | 2/2012 | Goldberg | |
| 2012/0070799 A1 | 3/2012 | Metcalf | |
| 2012/0292467 A1* | 11/2012 | Chen | A45D 27/225 |
| | | | 248/206.2 |
| 2013/0095508 A1 | 4/2013 | Campitelli et al. | |
| 2013/0197317 A1 | 8/2013 | Daniel et al. | |
| 2013/0204202 A1 | 8/2013 | Trombly et al. | |
| 2013/0317314 A1 | 11/2013 | Lampson | |
| 2013/0334069 A1* | 12/2013 | Fathollahi | H04B 1/3888 |
| | | | 206/37 |
| 2014/0055588 A1 | 2/2014 | Bangera et al. | |
| 2014/0121557 A1 | 5/2014 | Gannon | |
| 2014/0131412 A1 | 5/2014 | Canton | |
| 2014/0187870 A1 | 7/2014 | Weber | |
| 2014/0188095 A1 | 7/2014 | Weber | |
| 2014/0188107 A1 | 7/2014 | Weber | |
| 2014/0188128 A1 | 7/2014 | Weber | |
| 2014/0316310 A1 | 10/2014 | Ackermann et al. | |
| 2014/0343432 A1 | 11/2014 | Humayun | |
| 2014/0371542 A1 | 12/2014 | Goldberg | |
| 2014/0378940 A1 | 12/2014 | Lee | |
| 2015/0121557 A1 | 4/2015 | Pierce | |
| 2015/0134358 A1 | 5/2015 | Fisher | |
| 2015/0136922 A1 | 5/2015 | Shamsadov | |
| 2015/0186702 A1 | 7/2015 | Pletcher et al. | |
| 2015/0216618 A1 | 8/2015 | Jayaraj | |
| 2015/0245126 A1* | 8/2015 | Shaffer | H04R 1/1025 |
| | | | 381/74 |
| 2015/0306286 A1 | 10/2015 | Ross et al. | |
| 2017/0021113 A1 | 1/2017 | Goldberg | |
| 2018/0264205 A1 | 9/2018 | Bing | |

FOREIGN PATENT DOCUMENTS

| | | |
|---|---|---|
| CA | 2580792 | 10/2013 |
| CA | 3089618 A1 | 8/2019 |
| CN | 102473201 | 5/2012 |
| CN | 102473201 A | 5/2012 |
| CN | 103826686 | 5/2014 |
| CN | 103826686 A | 5/2014 |
| CN | ZL201080016524.X | 8/2014 |
| CN | 111757989 A | 10/2020 |
| EP | 2411074 | 2/2012 |
| FR | 2699083 A1 | 6/1994 |
| IL | 15355 | 9/2015 |
| JP | S6154832 | 4/1986 |
| JP | 548916 | 6/1993 |
| JP | 2002224183 | 8/2002 |
| JP | 2004129914 | 4/2004 |
| JP | 5549987 | 5/2014 |
| KR | 2012/0124742 | 11/2012 |
| KR | 2012/0124742 A | 11/2012 |
| RU | 2011141339 | 5/2013 |
| RU | 2523203 | 5/2014 |
| SU | 728859 A1 | 4/1980 |
| WO | 03024513 A1 | 3/2003 |
| WO | 2004000196 A1 | 12/2003 |
| WO | 2006/034324 | 3/2006 |

(56) References Cited

FOREIGN PATENT DOCUMENTS

| WO | 2008/042936 | | 4/2008 |
|---|---|---|---|
| WO | 2010/110823 | | 9/2010 |
| WO | 2010/111611 | | 9/2010 |
| WO | 2011005634 | A1 | 1/2011 |
| WO | 2012/163411 | A1 | 12/2012 |
| WO | 2012/0163411 | A1 | 12/2012 |
| WO | 2013/036625 | | 3/2013 |
| WO | 2013036507 | A1 | 3/2013 |
| WO | 2014/011740 | A1 | 1/2014 |
| WO | 2015/081181 | | 6/2015 |
| WO | 2016/178952 | A1 | 11/2016 |

OTHER PUBLICATIONS

Russian Decision on Granting for Russian application No. 2011141339/02 (061869) dated Mar. 19, 2014.
Japanese Office Action dated Jan. 7, 2014 for JP 2012-502291.
Decision to Grant for JP 2012-502291 dated Apr. 17, 2014.
Response for First Examination Report dated Mar. 20, 2019, for Indian Patent Application 4263/KOLNP/2011 (18 pages).
Written Opinion dated Mar. 14, 2019 for PCT/US19/015360, filed Jan. 28, 2019.
First Examination Report dated Jul. 2, 2019, for Indian Patent Application 712/KOLNP/2014 (9 pages).
Office Action dated Nov. 14, 2019 for U.S. Appl. No. 15/571,211, 18 pages.
For Chinese Patent Application No. 201680038977X (National Stage of PCT/US2016/029971): First Office Action dated Nov. 29, 2019 Search Report dated Nov. 19, 2019 (21 pages).
For Brazilian Patent Application No. BR112014005067-8 (National Stage of PCT/US2012/053744): Office action dated Oct. 15, 2019 (6 pages) Response filed Dec. 11, 2019 (34 pages).
First Office Action dated Jun. 23, 2022, for Canadian Patent Application No. 2,984,324.
First Office Action dated Jun. 28, 2022, for Canadian Patent Application No. 2,984,327.
Australian Patent Examination Report No. 1, dated May 5, 2014 for Patent application No. 20100229783, based on PCT/US10/028858.
Notice of Allowance for U.S. Appl. No. 13/253,572 dated Sep. 18, 2014.
Notice of Publication for HK Application No. 14108064.8 dated Sep. 26, 2014.
Notice of Allowance dated Mar. 30, 2020 for U.S. Appl. No. 15/571,211.
Supplementary European Search Report dated May 18, 2010 for Application No. EP05803150.
International Search Report published on Nov. 2, 2006, for PCT/US2005/33769, filed Sep. 19, 2005.
International Preliminary Report on Patentability published Mar. 20, 2007, for PCT/US2005/33769, filed Sep. 19, 2005.
Written Opinion published on Mar. 20, 2007, for PCT/US2005/33769, filed Sep. 19, 2005.
International Search Report dated Apr. 10, 2008, for PCT/US2007/80262, filed Oct. 3, 2007.
Written Opinion dated Apr. 10, 2008, for PCT/US2007/80262, filed Oct. 3, 2007.
International Preliminary Report on Patentability dated Apr. 7, 2009, for PCT/US2007/80262, filed Oct. 3, 2007.
International Search Report dated Jul. 16, 2010 for PCT/US2009/066033, published Sep. 30, 2010.
Written Opinion dated Jul. 15, 2010 for PCT/US2009/066033, published Sep. 30, 2010.
International Preliminary Report on Patentability dated Sep. 27, 2011 for PCT/US2009/066033, published Sep. 30, 2010.
International Search Report dated Dec. 21, 2010 for PCT/US10/28858 filed Mar. 26, 2010.
Written Opinion dated Dec. 20, 2010 for PCT/US10/28858 filed Mar. 26, 2010.

International Preliminary Report on Patentability dated Sep. 27, 2011 for PCT/US10/28858 filed Mar. 26, 2010.
International Search Report, Written Opinion dated Nov. 30, 2012 for PCT/US12/53744.
International Search Report and Written Opinion for PCT/US16/29938 dated Aug. 25, 2016.
Supplemental Response filed Oct. 10, 2013 for U.S. Appl. No. 13/179,674.
Office Action for U.S. Appl. No. 13/253,572 dated Sep. 17, 2013.
Notice of Allowance dated Oct. 21, 2013 for U.S. Appl. No. 13/179,674.
First Examination Report from Indian Patent Office, dated Oct. 25, 2018 for Indian Patent Application 4263/KOLNP/2011, National Stage of PCT/US2010/028858.
International Search Report, Written Opinion and International Preliminary Report on Patentability for International Application No. PCT/US2019/015360 filed Jan. 28, 2019.
Notice Prior to Allowance dated Dec. 31, 2014 for Israeli Patent Application No. 215355.
Supplementary European Search Report dated Jan. 7, 2015 for European Application No. 12829549.
European Communication dated Jan. 23, 2015 for European Application No. 12829549.
Notice of Allowance dated Feb. 13, 2015 for U.S. Appl. No. 13/253,572.
International Search Report and Written Opinion of the International Searching Authority mailed Feb. 25, 2015 for PCT/US2014/67587.
Response filed Nov. 14, 2016 in U.S. Appl. No. 14/343,085, filed Aug. 25, 2014, 13 pages.
International Search Report, dated Apr. 11, 2019, for PCT/US19/015360, filed Jan. 28, 2019.
Response to the notice prior to examination for Israeli application No. 215355 filed May 12, 2014.
Notice Prior of Allowance dated Jul. 16, 2014 for Israeli application No. 215355.
Ronald Melzack and Patrick Wall, What is Gate Control Theory?, about.com Psychology, 1960.
Jul. 21, 2013 response to Jan. 23, 2013 Office Action for Israel Application No. 215355.
Response dated Mar. 12, 2014 to Office Action dated Sep. 6, 2013 for EP Application 10756926.1.
Response dated May 12, 2014 to third Office Action for Chinese Patent Application No. 201080016524.X.
Notice of Publication for China application No. 201280043253.6 dated Jun. 5, 2014.
Final Office Action dated Apr. 16, 2015 for U.S. Appl. No. 13/259,409.
Response filed May 21, 2015 to Final Office Action dated Apr. 16, 2015 for U.S. Appl. No. 13/259,409.
Taiwanese Office Action dated May 15, 2015 for Application No. 101132425.
Notice of Allowance dated Oct. 21, 2013 for U.S. Appl. No. 13/179,674, filed Jul. 11, 2011.
Extended European Search Report dated Nov. 7, 2018 for Application No. 16789808.
Office Action dated Oct. 16, 2014 for U.S. Appl. No. 13/259,408.
Response Office Action filed Oct. 22, 2014 for Israeli Application No. 215355.
Notice of Allowance dated Oct. 2, 2014 for European Application No. 05 803 150.1-1651.
Notice of Allowance dated Oct. 6, 2014 for Mexican Application No. MX/A/2011/010069.
First Office Action dated Feb. 28, 2020 for Chinese Application No. 201680036948.X with partial translation.
Office Action dated Oct. 14, 2016 for Canadian Patent Application No. 2756890.
Office Action dated Jan. 15, 2016 for Canadian Patent Application No. 2756890.
Notice of Allowance dated Feb. 6, 2017 for U.S. Appl. No. 14/343,085.
Response to Office Action for U.S. Appl. No. 14/343,085, filed Nov. 14, 2016.

(56) References Cited

OTHER PUBLICATIONS

English translation of International Preliminary Report on Patentability dated Nov. 7, 2017 with Written Opinion for PCT/US2016/029971 filed Apr. 29, 2016.
Communication from European Patent Office dated Jan. 24, 2018 for Application No. 16789803.0-1122.
Office Action dated Jun. 21, 2018 from Canadian Intellectual Property Office for CA Appl. No. 2864411 (national stage of PCT/US2012/053774).
Office Action for U.S. Appl. No. 15/039,898 dated Apr. 13, 2018.
Office Action dated Jul. 20, 2016 for Japanese Patent Application No. JP2014-528700.
International Search Report and Written Opinion for PCT/US16/29971 filed Apr. 29, 2016.
Chinese Search Report dated Feb. 20, 2020 for Application No. 201680036948X and English translation.
Notice of Allowance for Canadian Application No. 2,756,890 dated Aug. 2, 2017.
Extended Search Report for EP19744408, dated Oct. 18, 2021.
International Preliminary Report on Patentability dated Nov. 7, 2017 with Written Opinion for PCT/US16/29971 filed Apr. 29, 2016.
International Preliminary Report on Patentability dated Nov. 7, 2017 with Written Opinion for PCT/US16/29938 filed Apr. 29, 2016.
Columbian Request for Technical Information dated Apr. 12, 2013 for application No. 11-140634.
Response to Columbian Request for Technical Information dated Jul. 15, 2013 for application No. 11-140634.
English translation of Japanese Office Action dated Jan. 7, 2014 for Japanese Patent Application No. JP2012-502291 filed on Sep. 20, 2012.
European Search Report (ESR) for EP application No. 107569266.1—PCT/US2010028858 dated Aug. 20, 2013.
For U.S. Appl. No. 13/253,572 Office Actions dated Sep. 17, 2013; Feb. 6, 2014 Responses filed Dec. 17, 2103; May 5, 2014.
Response dated Mar. 24, 2014 to Japanese Office Action for Application No. JP2012-502291 filed Sep. 20, 2012.
Office Action Summary dated Dec. 18, 2013 for MX/a/2011/010069.
International Search Report dated Dec. 13, 2012 for International Patent Application No. PCT/ US2012/053943 filed Sep. 6, 2012.
International Preliminary Report of Patentability (IPRP) published Mar. 12, 2014 and Written Opinion (WO) published Mar. 6, 2014 for International Patent Application No. PCT/ US2012/053943 filed Sep. 6, 2012.
Russian Decision on Granting a Patent for Invention filed on Mar. 26, 2010 for Patent Application No. RU2011141339 filed May 10, 2013.
Office action dated Jan. 23, 2013 for Israeli application No. 215355.
Response to office action dated Jul. 2013 for Israeli application No. 215355.
Response to Mexican Office Action dated Feb. 4, 2014 for Mexican Application No. MX/a/2011/010069 with English translation.
Office Action dated Mar. 31, 2014 for Mexican Application No. MX/a/2011/010069.
First Office Action for Chinese Application No. 201080016524X with English translation from Chinese associate dated Nov. 20, 2012.
Response to First Chinese Office Action for Application No. 201080016524X dated Jun. 5, 2013.
Second Office Action for Chinese Application No. 201080016524X with English translation from Chinese associate dated Jul. 25, 2013.
Response to Second Chinese Office Action for Application No. 201080016524X dated Dec. 5, 2013.
Third Office Action for Chinese Application No. 201080016524X with English summary from Chinese associate dated Feb. 27, 2014.
Notice of Publication dated Oct. 14, 2020 for Chinese Application No. 2020101000716320.
For U.S. Appl. No. 13/225,782: notice of allowance dated Sep. 5, 2013.
Office Action dated Jul. 12, 2016 for U.S. Appl. No. 14/343,085.
Response to Final Office Action, dated Jul. 18, 2016 for U.S. Appl. No. 13/259,408.
1 First Notification of Office Action dated Jul. 30, 2021 for Chinese Application No. 2019800140154 with translation.
For U.S. Appl. No. 13/225,782: restriction requirement dated Apr. 26, 2013 and response dated Jun. 26, 2013.
For U.S. Appl. No. 13/179,674; office action dated Oct. 16, 2012; response dated Jan. 16, 2013; final office action dated Mar. 18, 2013; response dated Aug. 19, 2013.
Communication dated Dec. 10, 2018 from European Patent Office with Supplementary European Search Report dated Nov. 30, 2018 for European Application No. EP 16789803.
Official action from European Patent Office for EP 05 803 150.1-1651 dated Nov. 16, 2011.
Response to official action from European Patent Office for EP 05 803 150.1 dated Mar. 26, 2012.
Second official action from European Patent Office for EP 05 803 150.1 dated Feb. 20, 2014.
Response filed with European Patent Office confirming applicant wishes to proceed for EP 05 803 150.1 dated Dec. 20, 2010.
Response to Mexican office action dated Jun. 9, 2014 for Mexican Patent Application No. MX/A/2011/010069.
Response filed Oct. 26, 2015 to Office Action dated Jun. 25, 2015 for U.S. Appl. No. 13/259,408.
Office Action dated Dec. 14, 2015 for U.S. Appl. No. 14/803,535.
Final Office Action dated Jan. 20, 2016 for U.S. Appl. No. 13/259,408.
Response filed Feb. 12, 2016 to Office Action dated Dec. 14, 2015 for U.S. Appl. No. 14/803,535.
Office Action dated Apr. 8, 2016 for Korean Patent Application No. 10-2011-7025440.
Response filed Jun. 8, 2016 for Office Action dated Apr. 8, 2016 for Korean Patent Application No. 10-2011-7025440.
Notice of Allowance dated Jun. 7, 2016 for U.S. Appl. No. 14/803,535.
International Preliminary Report on Patentability dated May 31, 2016 for PCT/US2014/067587.
Office Action dated Jun. 25, 2015 for U.S. Appl. No. 13/259,408.
Office Action dated Jun. 4, 2015 for Chinese Application No. 2012800432536.

* cited by examiner

HOLDER FOR MOUNTING A HANDHELD TOOL TO A SURFACE

FIELD OF THE DISCLOSURE

The disclosure relates to a system and method for vibrating a body part to reduce pain during piercing or medical treatment of the skin, and more particularly to applying vibration using a handheld tool with a vibrating tip having protrusions, and further to a stand for supporting the handheld tool.

BACKGROUND OF THE DISCLOSURE

Procedures for reducing pain when injecting a material into the body, removing a body fluid or body tissue, or otherwise piercing the skin or body tissue, include (a) placing a very cold material against the skin or flesh of the patient at the piercing site, (b) applying a topical treatment to the skin or flesh at the piercing site, which temporarily numbs the skin or flesh or (c) rapidly manually massaging the skin or tissue at the injection site while performing the injection.

SUMMARY OF THE DISCLOSURE

In an embodiment of the disclosure, a holder for mounting a hand tool to a surface comprises: a suction cup positionable upon the surface, the suction cup having a central area; a yoke connected to the central area, the yoke movable in a vertical direction relative to the surface, to distort the suction cup and create an area of low pressure between the suction cup and the surface, to secure the suction cup and yoke to the surface, the yoke including a cam engagement surface; a frame including a cradle shaped to receive and support the hand tool when a hand tool is placed onto the holder; a base; an extension connecting the base and the cradle; and a cam pin movable within the frame, the cam pin including a cam profile slideably engageable with the cam engagement surface of the yoke to push the yoke vertically away from the surface or allow the yoke to move towards the surface to increase or decrease the pressure between the suction cup and the surface.

In variations thereof, the cradle includes at least two flexible legs; the frame is fabricated from resilient plastic; and/or the cradle includes at least one of a projection or aperture, and wherein the hand tool includes the other of a mating aperture or projection, respectively, and wherein the projection and aperture mate when the device is positioned within the cradle, to thereby maintain a predetermined position of the hand tool within the holder.

In other variations thereof, the cradle is connected to the frame at a non-orthogonal angle with respect to the surface when the holder is connected to the surface using the suction cup; the pin moves along a plane parallel to the surface when the holder is mounted to the surface; the pin passes through one or more apertures in the frame, and wherein an end of the pin forms an exposed button which can be pressed to move the pin; the cam profile of the cam pin extends at a depth within the cam pin that varies along a longitudinal axis of the cam pin; the cam profile faces away from the surface when the holder is positioned upon the surface; the cam engagement surface faces toward the mounting surface when the holder is positioned upon the mounting surface; and/or the cam profile is oriented on a face of cam pin which faces away from the mounting surface when the holder is positioned upon the surface, whereby the cam engagement surface is in operative engagement with the cam profile as the pin is moved.

In still further variations thereof, the yoke is biased in the direction of the surface relative to the frame, when the holder is mounted upon the surface; the yoke is biased by a resilient bumper; the bumper is affixed to the frame along a portion of its length, leaving a free portion in engagement with the yoke; the yoke is co-molded to the suction cup; and/or the yoke is a different material than the suction cup.

In another variation thereof, the device further includes a container sized and dimensioned to house and limit free movement of: the device of claim 1, the hand tool, a lancet driver tool, a plurality of lancets, a blood glucose reader, and a container sized to contain glucose test strips.

BRIEF DESCRIPTION OF THE DRAWINGS

A more complete understanding of the present disclosure, and the attendant advantages and features thereof, will be more readily understood by reference to the following detailed description when considered in conjunction with the accompanying drawings wherein.

DETAILED DESCRIPTION OF THE DISCLOSURE

As required, detailed embodiments are disclosed herein: however, it is to be understood that the disclosed embodiments are merely examples and that the systems and methods described below can be embodied in various forms. Therefore, specific structural and functional details disclosed herein are not to be interpreted as limiting, but merely as a basis for the claims and as a representative basis for teaching one skilled in the art to variously employ the present subject matter in virtually any appropriately detailed structure and function. Further, the terms and phrases used herein are not intended to be limiting, but rather, to provide an understandable description of the concepts.

The terms "a" or "an", as used herein, are defined as one or more than one. The term plurality, as used herein, is defined as two or more than two. The term another, as used herein, is defined as at least a second or more. The terms "including" and "having." as used herein, are defined as comprising (i.e., open language). The term "coupled." as used herein, is defined as "connected." although not necessarily directly, and not necessarily mechanically.

The disclosure reduces pain to a patient being injected, for example with an anesthetic, serum, vitamins, vaccine, or other medically efficacious liquid. The disclosure can be easily and inexpensively utilized during a medical, veterinary or dental procedure to almost completely or substantially eliminate the pain attendant an injection as it punctures the skin or flesh of the patient. The disclosure also reduces pain due to any disturbance of the skin our underlying tissues, for example the pain which accompanies puncture of the skin associated with removal of fluids from the body. Examples include while removing blood for a glucose test or other blood analysis; during a puncture associated with treatment of the skin, such as acne or blisters; and for other fluid withdrawals, for example during phlebotomy, paracentesis, aspiration, or synovial fluid withdrawal.

The disclosure provides a disposable tip and a hand-held apparatus, which in an embodiment has the form of an instrument 10, for vibrating a skin or tissue area. In various embodiments, a vibrating end or tip 40 contacts at least two skin or tissue areas, or a circular skin or tissue area, immediately at an injection site, puncture site or site of a painful contact, and does so while the potentially painful therapeutic procedure takes place. Pain can be caused by injection, for example of a liquid anesthesia, serum, vitamins, vaccine, or other medical or dental efficacious material, into the skin or tissue at the injection site. Typically, a region of interest for a dentist can be the entire oral mucosa area and underlying bone, whereas the region of interest for a medical doctor can be the whole body and underlying bone. For a non-medical professional, the region of interest could be the fingertip or other area a lancet will prick to obtain blood for a glucose measure, for example. The disclosure is applicable to any of these situations, for any area of the body.

The method of the disclosure consists in vibrating tissue of a human or animal in proximity to a preselected puncture or injection site on the human or animal body while simultaneously puncturing or injecting by a needle or like instrument a liquid at the preselected site. The vibration can be effective if transmitted to a circular or other shaped area of body tissue, which can include bone underlying skin at a puncture or injection site, and particularly on opposite sides of the site.

Background helpful in understanding the disclosure can be found in the following documents, the contents of each of which are hereby incorporated herein by reference in their entirety:

U.S. Patent Application 60/661,497 filed Sep. 20, 2004;
U.S. Patent Application 60/707,754 filed Aug. 12, 2005;
PCT Application PCT/US05/33769 filed Sep. 19, 2005;
U.S. Patent Application 61/163,945 filed Mar. 27, 2009;
PCT Application PCT/US09/66033 filed Nov. 29, 2009;
PCT Application PCT/US10/28858 filed Mar. 26, 2010;
U.S. patent application Ser. No. 13/179,674 filed Jul. 11, 2011, now U.S. Pat. No. 8,668,664;
U.S. patent application Ser. No. 13/225,782 filed Sep. 6, 2011, now U.S. Pat. No. 8,662,952;
U.S. patent application Ser. No. 13/253,572 filed Oct. 5, 2011;
PCT Application PCT/US12/53744 filed Sep. 5, 2012;
U.S. Patent Application 61/531,264 filed Sep. 6, 2011;
PCT Application PCT/US12/53943 filed Sep. 6, 2012;
U.S. Patent Application 61/909,544 filed Nov. 27, 2013;
PCT Application PCT/US14/67587 filed Nov. 26, 2014;
U.S. Patent Application 62/155,769 filed May 1, 2015;
U.S. patent application Ser. No. 14/803,535 filed Jul. 20, 2015;
U.S. Patent Application 62/208,860 filed Aug. 24, 2015;
International Patent Application Number PCT/US2016/029971 filed Apr. 29, 2016, and published as WO2016/178952 A1; and
International Patent Application Number PCT/US2016/029938 filed Apr. 29, 2016, and published as WO/2016/178941 A1.

Figures 12, 13:
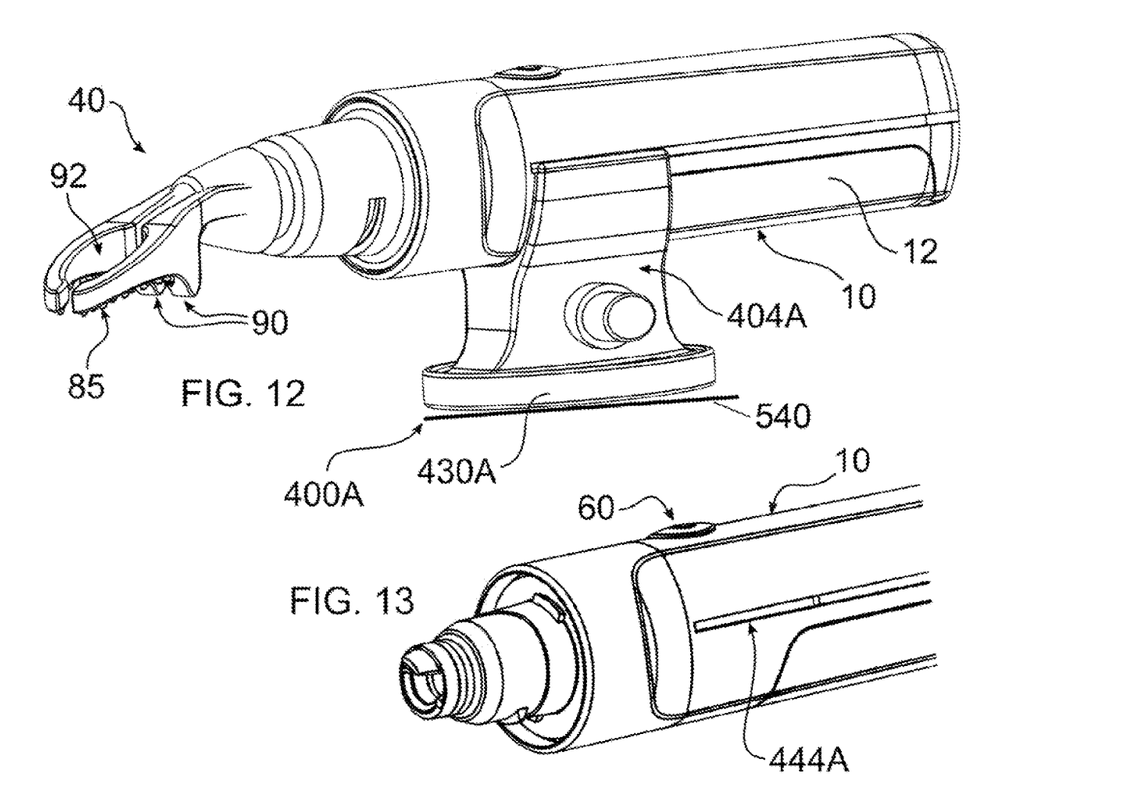
FIG. 12 depicts a perspective side view of an instrument and holder of the disclosure.
FIG. 13 depicts the instrument of FIG. 12, with a vibratory tip and holder removed.
Figure 14:
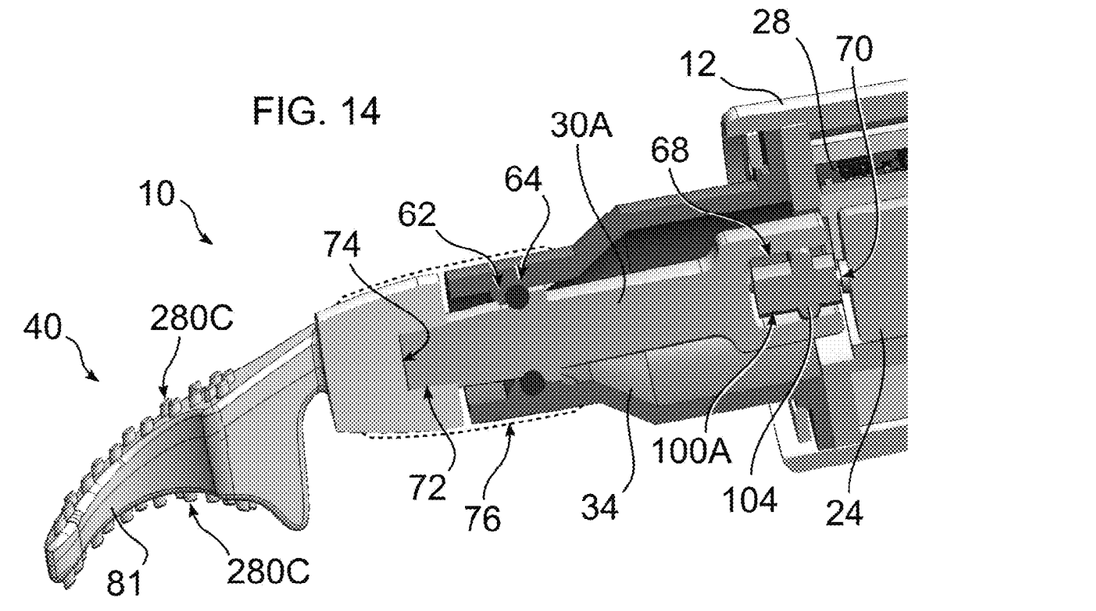
FIG. 14 depicts a cross-section of an alternative device of the disclosure, bisected approximately vertically.
Figures 15, 16:
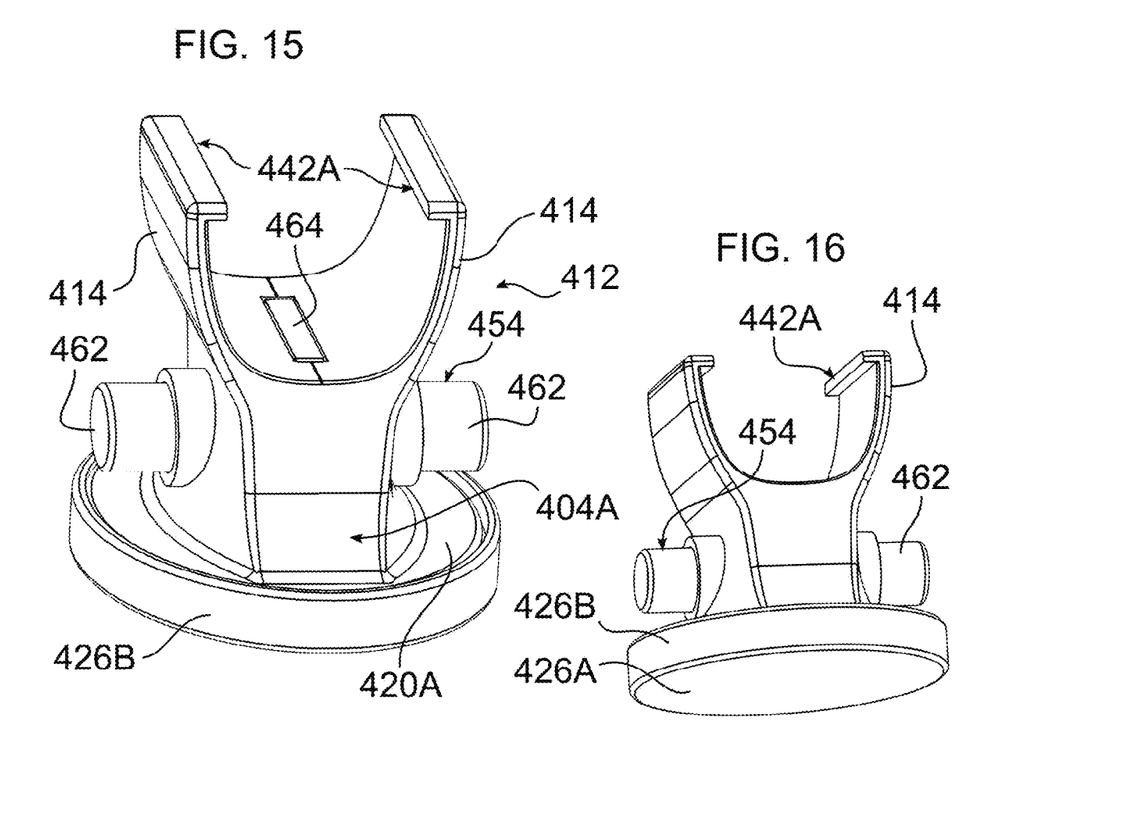
FIG. 15 depicts a top front perspective view of the holder of FIG. 13.
FIG. 16 depicts a rear perspective view of the holder of FIG. 13.
Figure 17:
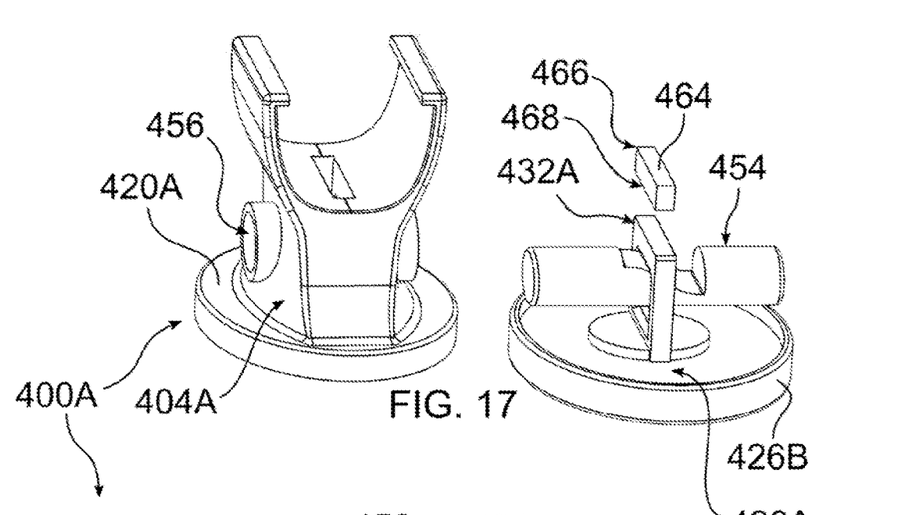
FIG. 17 depicts an exploded view of the holder of FIG. 15, with the suction cup, yoke, and cam pin removed.
Figure 22:
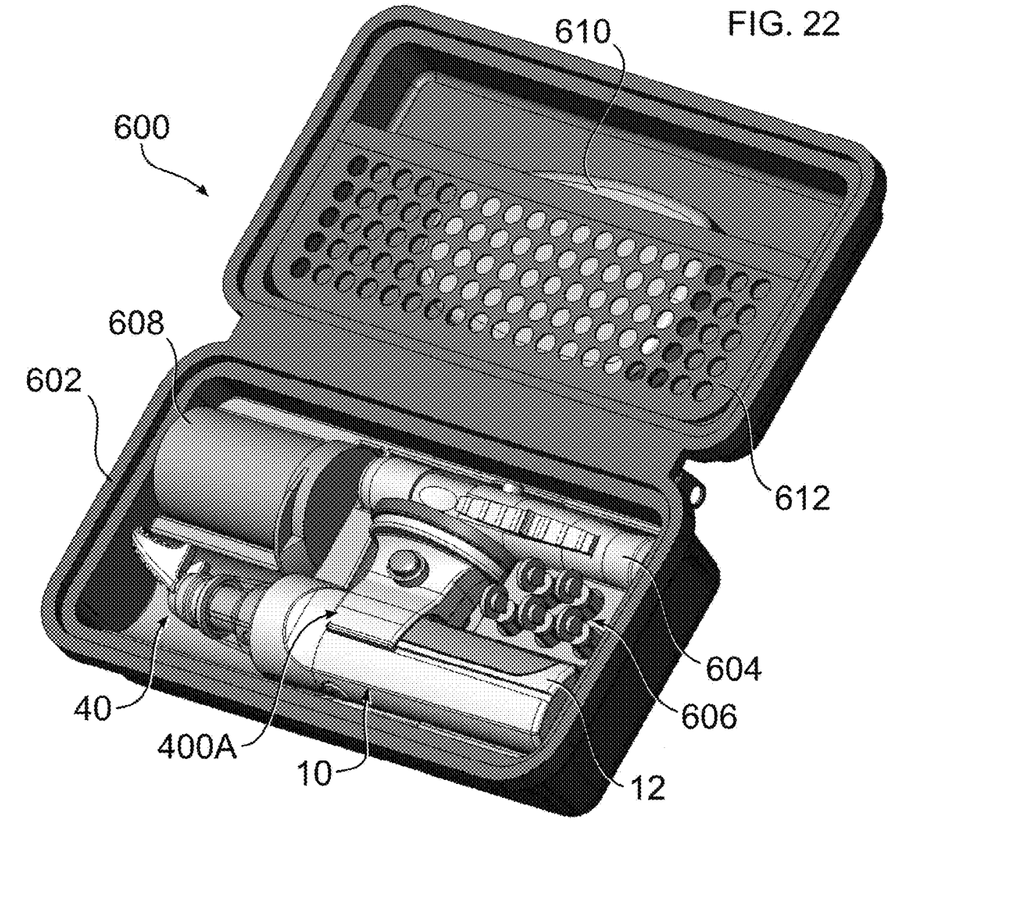
FIG. 22 depicts a kit containing an instrument of the disclosure and associated therapeutic elements.

With reference to FIGS. 12, 14, and 22, an instrument 10 includes a handle 12 which contains a battery (not shown), and means to charge the battery, for example a cable, plug, or induction coil (not shown). A control circuit 28 is disposed within handle 12, and controls the operation of a motor 24. A switch 60 (FIG. 13) is pressed by a user of instrument 10 to cause the motor to start. A cam 100A is connected to the motor output, and causes pivotal movement of a vibration transmitting rod 30A about a pivot at O-ring 64. A patient contacting tip 40 is connected to an end of rod 30A opposite cam 100A, and vibrates due to the eccentric path of cam 100A. Tip 40 can have a smooth or rough surface, can include ridges or other shapes, or can include one or more nubs 280 positioned on a front, end, or back surface thereof. Nubs 280 facilitate transmission of vibration into the patient, which affects the nervous system of the patient to reduce a sensation of pain of the therapeutic procedure during vibration.

Handle 12 is shaped to be grasped by the hand of the user, thereby enabling instrument 12 to be used as a hand tool. A holder 400A can be used to store or temporarily hold instrument 10, or can be used to hold instrument 10 during a therapeutic procedure.

Tip 40 can be either permanently or removably mounted to handle 12. In an embodiment, a twist lock connection is used to mount tip 40. Alternatively, a snap-fit, magnetic, threaded connection, or interference fit, for example, can be used to releasably secure tip 40 to a remainder of instrument 10.

In an embodiment of the disclosure, instrument 10 is fabricated with a minimal or no use of threaded fasteners, as these can tend to be vulnerable to loosening when instrument 10 is used to produce vibration at particular frequencies. This effect can be mitigated by using a thread locking compound or material. In an embodiment, motor 24 is mounted within handle 12 by being soldered or welded to metallic tabs which are adhered or co-molded with an interior portion of handle 12. Likewise, battery contacts and other electrical or mechanical contacts can be inserted into retaining channels formed within a body or other component of handle 12. Instrument 10 can further be improved by using lithium or state of the art batteries which reduce weight and/or provide an extended run time when charged.

In various embodiments of the disclosure, re-use of an end piece such as a vibrating tip of the instrument can be prevented, to avoid cross-contamination between patients. In one embodiment, the tip is broken when removed. In another embodiment, electromagnetic communication is established between an electronic tag on a tip and an electronic circuit within the body of the instrument. In this manner, a use count and validation of the tip can be monitored, and activation of the instrument can be disabled if the tip should be replaced after a period of time, or a predetermined number of uses, which are indicative of potential reuse between patients. In other embodiments, the tip can be re-used a number of times.

The embodiment disclosed herein is a tool for relieving pain associated with an injection, or any other piercing of the skin. For example, in addition to injections, the disclosure applies to other pain inducing procedures applied to any body tissue, such procedures including cauterizing, application of laser light, application of chemicals, or insertion of sutures, clips, or staples, or to pierce the skin to withdraw a sample of a body fluid. Further, it should be understood that the disclosure can be used to control the use of any tool tip, whether used in dentistry, general medicine, or within an industrial application, for example a grinding or boring machine tool tip, or other end effector.

Figures 1, 2, 2A, 2B:
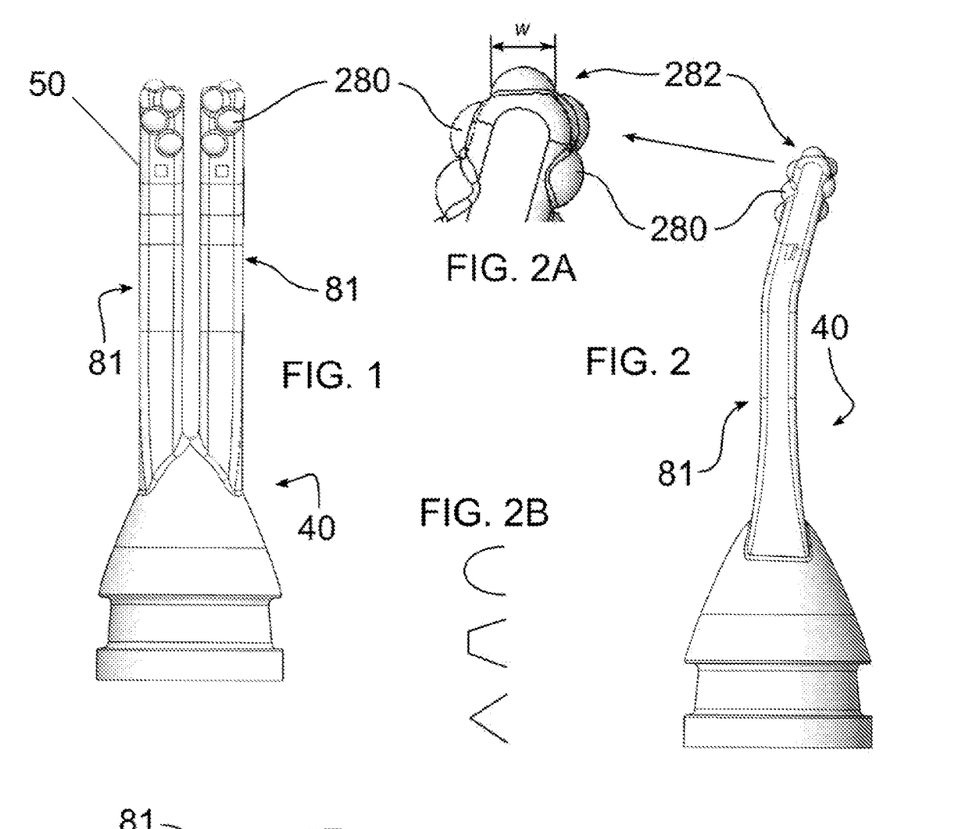
FIG. 1 depicts a top view of a vibratory tip of the disclosure, having a plurality of nubs.
FIG. 2 depicts a side view of the tip of FIG. 1.
FIG. 2A depicts a detail view of a distal end of the tip of FIG. 2.
FIG. 2B depicts alternative cross-sectional profiles for nubs of the disclosure.

Referring now to FIGS. 1-2, a tip 40 is adapted to attach to an instrument 10, to transmit vibration to a distal tip portion 50, to thereby transmit the vibratory energy to the patient through contact with the treatment area. The vibration caused by contact with a device of the disclosure produces a therapeutic effect which results in a diminution of the sensation of pain associated with a therapeutic procedure, for example a skin puncture or excision, or a treatment of body tissue.

Tip 40 can have any of a variety of shapes, some of which are disclosed herein, which are adapted or adaptable to the shape and dimension of body tissue to be made less sensate to pain by a device of the disclosure. Such shapes can include for example pronged, ring shaped, and adapted to engage a finger. The tip can likewise have RFID or wireless features, and/or tearing or other reuse controlling features. For example, an RFID feature can be used to count, for example by a computing circuit within handle 12, a number of times a tip 40 has been used, for example more than once, to prevent cross contamination between patients, and to maintain consistent performance. Tip 40 can include an overmold, and/or can be molded with different layers and components, to present a smooth external surface, and to prevent the intrusion of body fluids or other debris into instrument 10.

Figures 3, 4:
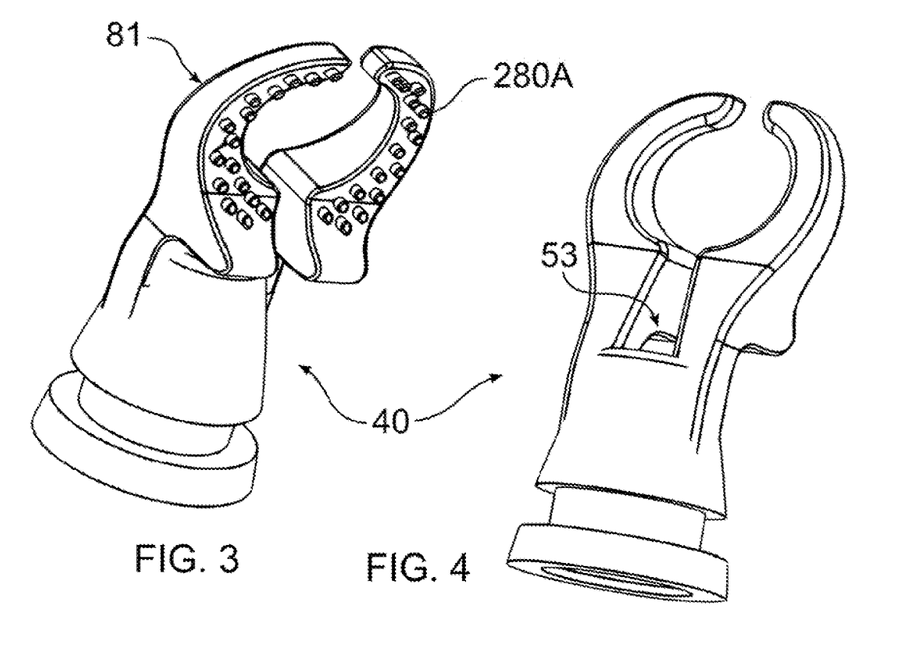
FIG. 3 depicts a perspective bottom view of an alternative vibratory tip of the disclosure, including an alternative arrangement of nubs.
FIG. 4 depicts a top view of the tip of FIG. 3.
Figure 5:
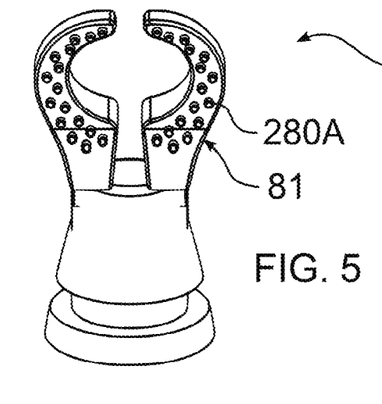
FIG. 5 depicts a distal end perspective view of the tip of FIG. 3.
Figure 6:
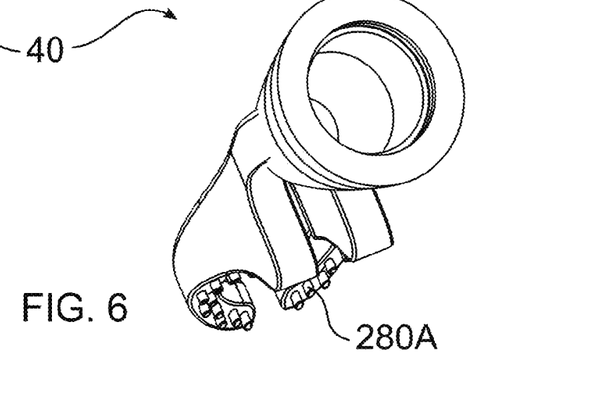
FIG. 6 depicts a proximal end perspective view of the tip of FIG. 3.

With reference to FIG. 2A, tip 40 disclosed herein is additionally provided with nubs 280 having a small cross-sectional area with "w" relative to the cross-sectional area of an associated arm 81. For example, w can be, for example, typically 0.25 mm to 3 mm, or as small as 0.05 and as large as 5 mm depending upon the size of the patient being treated and the cross-sectional area of arm 81, and may be further provided with a pointed distal profile, a rounded distal profile as shown, an alternate shaped profile, or a combination of profiles. Non-limiting examples of oval, polygonal, and pointed nub 280 profiles are shown in FIG. 2B. In FIGS. 3-4, the profile of nubs 280A are truncated cylinders, which can have a flat distal end profile as shown, or which can have a distal end profile that forms an angle with respect to a longitudinal axis of the nub 280A.

Referring again to FIGS. 1-2, it may be seen that nubs 280 are positioned on two or more sides of arm 81, as may be the case with any other nub shapes shown or described herein. In FIGS. 1-2, nubs 280) are positioned on opposite sides and upon a distal end 282 of arms 81, however they may be positioned on all sides, or any number of surfaces of arm 81.

Without being bound to any particular theory, the inventors have found that nubs 280/280A (hereinafter all nubs may collectively be referred to as 280) intensify the pain-relieving characteristics of tip 40 and instrument 10. For example, the narrower distal shape of nub 280 may server to direct the vibratory energy more deeply into the skin. Further, the increased instance of points of contact with the skin may increase vibratory contact. Likewise, a combination of deeper skin penetration of vibration over a relatively greater number of contact points may result in an overall greater transfer of vibratory energy into the patient at the site of application of nubs 280. Again, without being bound to a particular theory, a higher number of nerve sensors may be occupied conducting sensed vibratory contact, resulting in fewer nerve sensors carrying sensed pain, or nerve sensors may have a diminished capacity to convey sensed pain due to signals being conveyed relating to vibratory contact.

Additionally, by positioning one or more nubs 280 upon different sides of arm 81, different parts of the patient's anatomy may be subjected to vibratory energy. For example, in the mouth, it would be possible to stimulate the gingivae and cheek simultaneously. It should be understood, however, that a different but beneficial therapeutic benefit can be obtained by providing a tip 40 without nubs 280.

Figures 7, 8, 9:
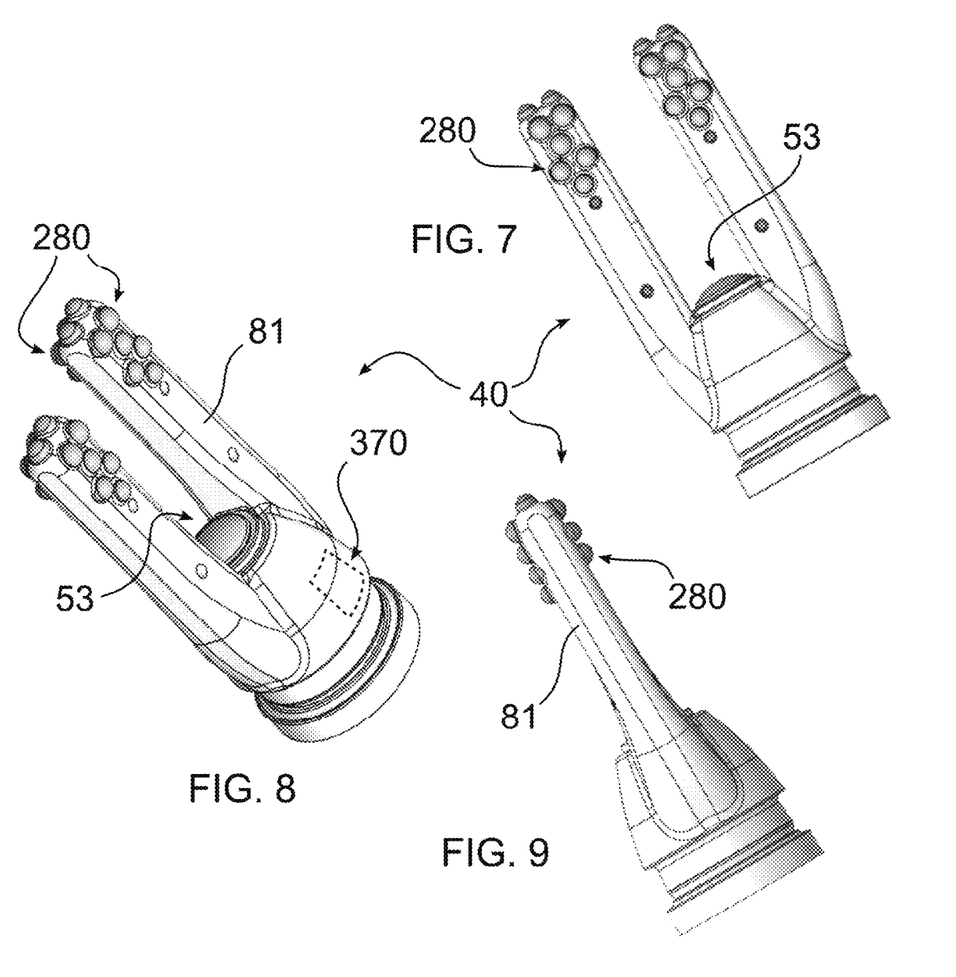
FIG. 7 depicts a perspective top view of an alternative vibratory tip of the disclosure, including an alternative arrangement of nubs.
FIG. 8 depicts a top perspective view of the tip of FIG. 7.
FIG. 9 depicts a side perspective view of the tip of FIG. 7.
Figure 10:
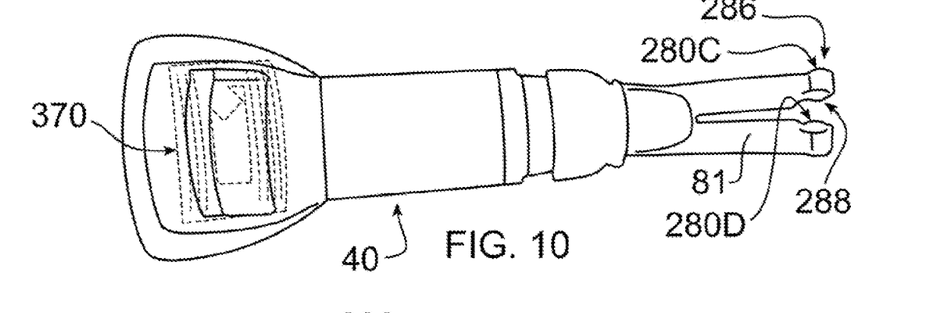
FIG. 10 depicts a top view of a further alternative vibratory tip of the disclosure, including another arrangement of nubs.

In the embodiment of FIGS. 7-9, as with the embodiment of FIGS. 1-2, a plurality of nubs 280C are provided, positioned to extend from the front and back of arm 81. In the embodiment of FIG. 10, there is only a single nub 280C provided at each face, on each arm 81. The presence of a single nub 280C per face of arm 81 can serve to focus vibratory energy over a very small area, which may provide a different and useful effect, depending upon a particular therapeutic application, with respect to the multiple nubs 280 per face, as shown in FIGS. 1-2. In a variation of FIG. 10, nub 280C may be omitted on the front face 286 or rear face 288. As can be seen in FIGS. 7-9, arms 81 are spaced at opposite sides of gap, or alternatively adjacent a central lens 53 from which light is emitted.

In FIGS. 7-9, it may be seen that nubs 280 may alternatively have the same size and shape whether they are positioned on the front, end, or back of arm 81. While a plurality of numbs 280 are shown in FIG. 7-9, it should be understood that a single nub 280 can be provided upon any one of the front, end, and side portions of arm 81.

In at least some embodiments of tip 40, extension arms 81 can be bent to facilitate a therapeutic procedure using instrument 10. For example, arms 81 can be bent to alter a fit between a cheek and gums, or otherwise bent to better fit the anatomy of a specific patient. In an embodiment, a wire or other stiff frame, for example of metal, can be placed into a mold prior to injection of overmolded thermoplastic or other material. Alternatively, the molded material can be selected from a material which at least substantially retains a shape once bent, and no underlying wire or frame is needed.

As can additionally be seen in FIGS. 7-8, a light may be emitted at a location or lens 53, and an RFID tag 370) can optionally be provided upon or within tip 40.

Figure 11A:
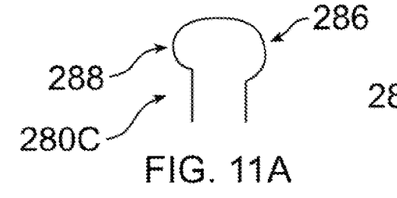
FIG. 11A depicts a side view of an end of the extension arm of FIG. 10.
Figure 11B:
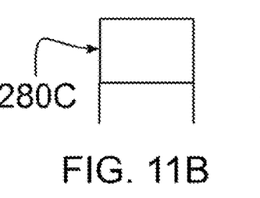
FIG. 11B depicts a back view of the extension arm end of FIG. 10.
Figure 11C:
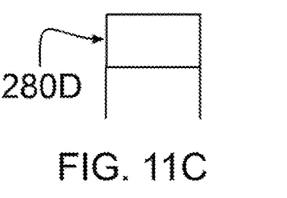
FIG. 11C depicts a front view of the extension arm end of FIG. 10.

In FIGS. 10-11, for each arm 81, nub 280C has a curvature extending across a front face portion 286 (FIG. 11A, 11B). Similarly, a nub 280D extends across a rear face portion 288 (FIGS. 11A, 11C). In an embodiment, a size and location of a radius of the nubs 280C at the front and rear facing portions 286, 288 define curves having differing radius width and radial centers. In this manner, a shape of nubs 280 can be targeted very specifically to the anatomy typically found at a target usage site.

FIG. 14 depicts a cross-section of an instrument 10 in accordance with the disclosure, which has an alternative tip engagement configuration with respect to that shown in FIGS. 12 and 13. In FIG. 14, a vibration transmitting rod 30A transmits motion produced within handle 12 to vibration along an exterior surface of tip 40. Rod 30A can optionally transmit light as well as vibration, for example by being fabricated with a light transmissive material or having a light channel, or by producing light within, to a lens 53 (not shown in FIG. 14).

A base of rod 30A includes a base recess 68 into which an eccentric cam 100A rotates. An electric motor 24 is affixed to handle 12, and has an output shaft 70 which is connected to circular cam 100A having eccentric cam lobes 104. Motor 24 can be controlled by an electronic circuit 28, and can be activated by a switch 60 (FIG. 13), which either mechanically completes an electrical connection to motor 24, or which signals to circuit 28 that it is desired to start motor 24.

In an embodiment arms 81 have been found to produce a therapeutic pain relieving benefit if caused to vibrate at an amplitude of 0.1 to 5 mm, although a greater or lesser amplitude is possible, if a therapeutic procedure indicates such a need. It should be understood that amplitude will vary whether arms 81 are suspended in air, or pressed with a light pressure on the skin. The foregoing values are for amplitude based upon a light pressure upon the skin. Amplitude in air may be greater, for example 2.0-2.5 mm, which results in amplitude of 1.0-1.5 mm with light pressure upon the skin. Greater amplitude can be created, for example, by using a lower frequency and increasing power to motor 24. A frequency within the range of 100 to 300 Hz has been found to be therapeutically beneficial for reducing pain, although a slower or faster frequency can be effective.

Without being bound to any particular theory, it appears that by cycling or pulsing as described, the brain does not get accustomed to, or habituate to the vibration, and thus the vibrations remain effective. Patterns and durations of pulsing or cycling can be used, as best determined by the practitioner as observed to reduce habituation to the vibration among various patients or patient demographics. To this end the electronic circuit 28 can be used to control pulsing to obtain a desired on/off duty cycle. The medical practitioner can apply vibration using instrument 10 for a period prior to potentially causing pain, for example for a period of 1 to 90 seconds, and can continue to apply pressure after treatment, also for a period of 1 to 90 seconds, depending on the body tissue affected, tip shape selected, and the type of treatment, for example.

In an embodiment for one type of therapeutic procedure, motor 24 is energized using one or more lithium batteries. The vibration at the free ends of arms 81 can vary from about 1.0 mm to about 3.0 mm, in an embodiment advantageously 1.5 mm to 2.0 mm. In some embodiments, the vibrating tip is placed on or near the location for anywhere from around 3 seconds to around 15 seconds, with the vibration continually applied. In other embodiments, a duty cycle of about 1.05 seconds with on pulsing of about 1 sec. and off of about 0.05 seconds is used. Depending on a patient's physiology and the desired application, at least one of the vibration amplitude and duty cycle can be varied to be more effective.

A nozzle 34 is affixed to handle 12, and includes an internal support 62 for an O-ring 64. Vibration transmitting rod 30A passes through and is pivotably supported by O-ring 64. As cam 100A rotates, base recess moves in an orbit about output shaft 70, which orbital motion is translated to a distal end 72 of vibration transmitting rod 30A via pivoting about O-ring 64. Distal end 72 inserts into a recess 74 within tip 40. Rod 30A and tip 40 can be attached by any other means, including alternatively providing an extension on tip 40 which inserts into a recess in distal end 72, or distal end 72 and tip 40 can be attached by a fastener, magnet, or other means. Such attachment means is advantageously releasable, so that a new tip 40 can be used for each new patient or treatment.

An overmold or sleeve 76 can be provided to prevent passage of debris between an exterior of instrument 10 and an interior of nozzle 34. Tip 40 can be separated from instrument 10 together with sleeve 76, nozzle 34, and transmitting rod 30A. Alternatively, tip 40 can be removed together with or separated from sleeve 76, leaving the remaining components in connection with instrument 10, or may be removed together with various combinations of these elements. In an embodiment, nozzle 34 forms a twist-lock connection with handle 12, whereby tip 40 can be removed or attached to instrument 10 by radial rotation of tip 40 including nozzle 34 with respect to handle 12.

With reference to FIGS. 12 and 15-20, an instrument 10 cooperative with a tip 40, is supported by a mounting base or holder 400A. A suction cup 430A is positioned at a one end of a base extension 404A, and an instrument holder 412 is positioned at an opposite end of extension 404A. Holder 400A can be sized and shaped to releasably and securely retain any instrument 10 of the disclosure as described herein. FIG. 13 illustrates an embodiment of instrument 10 without a tip 40 attached, in accordance with one embodiment of tip 40.

Instrument holder 412 is shaped to slidingly and releasably retain handle 12 of instrument 10, and can form a tapered profile which mates with a tapered profile of handle 12, to enables insertion of instrument 10 to a desired predetermined extent, whereby a sufficient portion of handle 12 extends from holder 412 to enable handle 12 to be easily grasped and pulled to remove instrument 10. As an alternative to a tapered fit, handle 12 can be shaped to contact a surface of instrument 10 to prevent insertion beyond a desired predetermined extent.

In addition, or as an alternative to the foregoing, holder 412 and handle 12 can be provided with mating detent portions, such as a protrusion 442A on one part, and a recess 444A on another, which engage when instrument 10 has been inserted sufficiently. In the embodiment shown, protrusion 442A is disposed on one or more of a resilient cradle arm 414, integrally molded with holder 412. Recess 444A is disposed within handle 12, although it should be understood that a recess can be provided within holder 412, and a protrusion can be provided upon handle 12. When instrument 10 is inserted, cradle arm 414 bends to enable protrusion 442A to be displaced by handle 12. When protrusion 442A is aligned with recess 444A, cradle arm 414 pushes protrusion 442A into recess 444A. An alignment of protrusion 442A and recess 444A can be achieved by mating surfaces in an interior surface of holder 412, and corresponding mating exterior surfaces of instrument 10, which contact each other to mutually guide and orient instrument 10 as it is inserted into holder 412.

While a vibratory instrument 10 is illustrated and described, it should be understood that holder 400A of the disclosure can be used with any hand tool, wherein a cradle formed of one or more cradle arms 414 is adapted to the shape of the particular hand tool, and wherein protrusions 442A or recess 444A are provided on the adapted cradle and hand tool, respectively.

Holder 412 includes two opposed cradle arms 414, 416 which can be formed with a resilient material, whereby cradle arms 414/416 can bend to enable engagement and disengagement of the mating portions 442A, 444A. Alternatively, resilient cradle arms 414, 416 can be formed to define, when relaxed, an interior diameter which is smaller than a diameter of instrument 10 or handle 12, whereby a wedging force is achieved when instrument 10 has been inserted, which causes instrument 10 to be securely retained between cradle arms 414 when sufficiently inserted.

Holder 412 can further be disposed at an angle with respect to a plane defined by a bottom of suction cup 430A, which is intended to be secured upon a mounting surface 540 upon which holder 400A is to be mounted. In this manner, gravity can be employed to retain instrument 10 within holder 412. In the embodiment shown, an angle of 15 degrees is formed, although any angle can be used, for example anywhere from 10 to 30 degrees, although any angle between zero and vertical, inclusive, can be used in accordance with the disclosure. In an embodiment, the angle can be selected by rotating holder 412 about a pivot (not shown) which connects holder 412 to base extension 404A.

Base extension 404A increases a height of holder 412 above a surface to which device stand 400 is mounted. In this manner, tip 40 does not contact the surface when instrument 10 is in holder 412, and handle 12 is spaced from the surface to be easily grasped by a hand.

With reference to FIGS. 15-20, suction cup 430A is positioned beneath a circular base 420A, the latter being attached to base extension 404A. Suction cup 430A includes a planar suction base 426A, and a peripheral wall 426B extending vertically, with respect to a mounted position, from suction base 426A, which surrounds and orients circular base 420A with respect to suction cup 430A.

Figures 18, 19, 20:
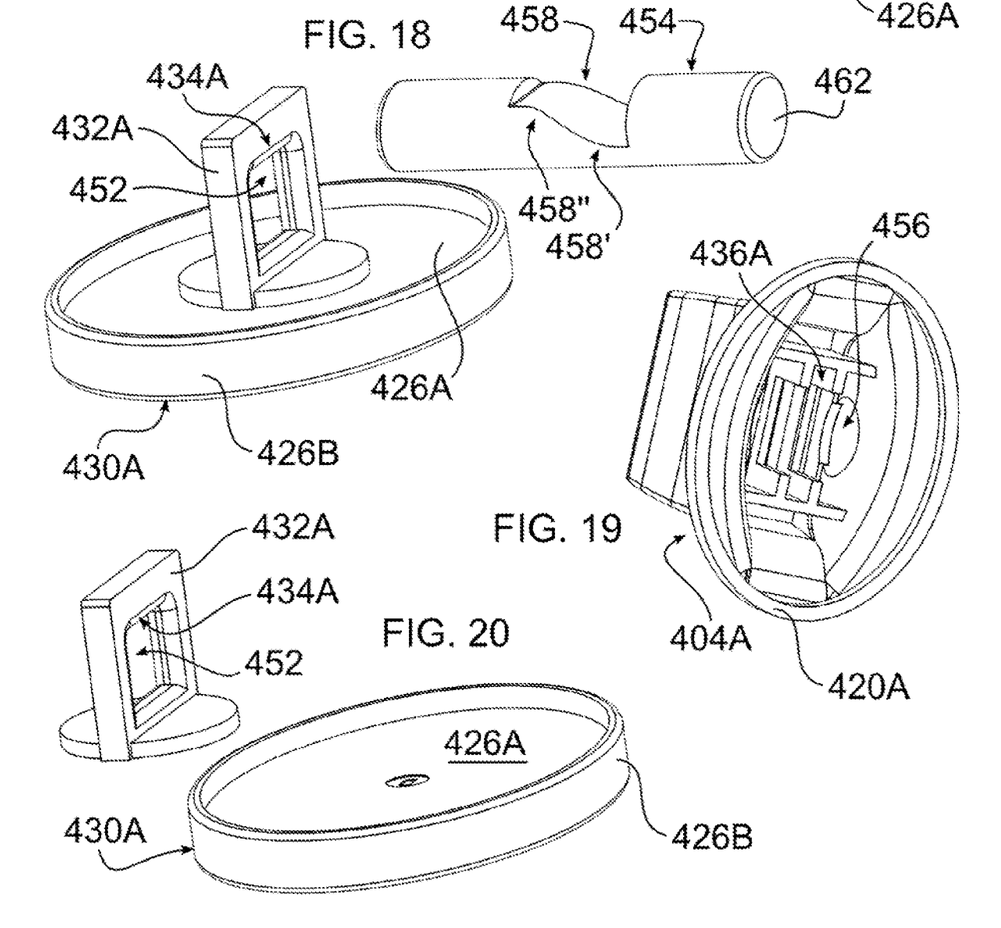
FIG. 18 depicts an exploded view of internal element of the holder of FIG. 17.
FIG. 19 depicts a bottom view of the holder of FIG. 17, with internal elements removed.
FIG. 20 depicts a perspective view of a suction cup of the disclosure, with an unattached yoke.

Suction cup 430A is connected at a center of suction base 426A to a yoke 432A, the latter forming an aperture 452. In FIG. 18, yoke 432A and suction base 426A are integrally formed or co-molded together. FIG. 20 illustrates that yoke 432A and suction base 426A can alternatively be formed as separated parts joined by any known method, such as a fastener, including adhesive.

A cam engagement surface 434A is provided upon yoke 432A, facing towards aperture 452. Yoke 432A is inserted within a channel 436A formed within base extension 404, to be slideable vertically with respect to a mounting plane of holder 400A. Suction cup, through attachment to yoke 432A, has the ability to swivel or flex laterally and to thereby lie flat upon a mounting surface 540 adjusting for irregularities in the shape of parts or in mounting surface 540. In an embodiment, cam engagement surface 434A faces toward the mounting surface when holder 400A is positioned upon the mounting surface.

A cam pin 454 passes through yoke aperture 452, and is slideably supported by opposed apertures 456 formed in base extension 404. Cam pin 454 includes a cam profile 458 which engages yoke cam engagement surface 434A, to raise and lower yoke 432A vertically, as cam pin 454 is moved horizontally, with respect to a plane of a mounting surface of holder 400A. When a relatively deep area 458' of cam profile 458 engages cam engagement surface 434A, suction base 426A is permitted to form a planar shape, and suction between suction base 426A and a mounting surface 540) (not shown) is released, enabling holder 400 to be removed from mounting surface 540). In an embodiment, cam profile 458 extends at a depth within cam pin 454 that varies along a longitudinal axis of cam pin 454. In an embodiment, when the cam engagement surface 434A faces toward the mounting surface, cam profile 458 is oriented on a face of cam pin 454 which faces away from the mounting surface when holder 400A is positioned upon the mounting surface, whereby cam engagement surface 434A is driven into operative engagement with cam profile 458.

When suction cup 430A is in planar, sealing contact with mounting surface 540, and cam pin 454 is moved to gradually place a relatively shallow area 458" of cam profile 458 into engagement with cam engagement surface 434A. In so doing, a center area of suction base 426A is pulled vertically, distorting the suction base to form an area of low pressure between suction base 426A and the mounting surface. More particularly the distorted area can have, for example, a conical or tented shape (not shown), with the vacuum present within the tented shape, thereby attaching suction cup 430A to mounting surface 540, and affixing holder 400 to mounting surface 540. Opposed ends of cam pin 454 form buttons two buttons 462, either of which extend from base extension 404A, and which may alternately be pushed to move cam pin 454 into engagement with either deep or narrow area 458', 458", to create or release suction to engage or release holder 400.

A resilient bumper 464 is positioned to have an upper end 466 secured within base extension 404A, and a lower end 468 that freely extends within base extension 404A to lie in deformable contact with an upper portion of yoke 432A. Bumper 464 functions to continuously urge cam engagement surface 434A into contact with cam profile 458, and to press upon instrument 10 when suction cup 430A is engaged with a mounting surface 540. In an embodiment, a portion of yoke upper end 466 can be secured within base extension 404A to freely extend into a space between cradle arms 414, whereby when instrument 10 is inserted into holder 400A, upper end 466 resiliently engages instrument 10, for example by pressing upon handle 12 or other portion of instrument 10, to contribute to securely holding instrument 10 within holder 400A and in contact with cradle arms 414,416, whereby instrument 10 may be used 'hands free' without excessive movement or displacement due to vibration. Another form of biasing element can be used for bumper 464, including for example a coil or leaf spring, secured in a manner as described above.

Holder 400A can be fabricated of any material, for example metal, wood, plastic, including injection molded plastic, or composite material. Plastic is advantageous as it can be used in a clinical environment, and can be machine washed or wiped with disinfectant cleaners without being damaged. Further, plastic can be selected to be inherently resilient, thereby facilitating the formation of resilient cradle arms 414. However, other materials can also be used for some or all of holder 400A, in particular metal, including shape metal alloys, for example. Non-limiting examples include thermoplastics such as Acrylic, ABS, Nylon, PLA, Poly benzimidazole, Polycarbonate, Polyether sulfone, Polyetherether ketone, Polyetherimide, Polyethylene, Polyphenylene oxide, Polyphenylene sulfide, Polypropylene, Polystyrene, Polyvinyl chloride, and Teflon.

Suction cup 430A can be fabricated from any of the foregoing materials which are soft and pliable at room temperature, further including rubber or a polymeric analog, such as a thermoplastic elastomer, which can be a Styrenic block copolymers (TPE-s), Thermoplastic olefins (TPE-o), Elastomeric alloys (TPE-v or TPV), Thermoplastic polyurethanes (TPU), Thermoplastic copolyester. Thermoplastic polyamides. Other materials can include natural or synthetic rubber, or silicone based materials, as understood within the art. Similar materials can be used for bumper 464.

Holder 400A can be fabricated using any known method which can produce parts as a unit, as shown, or in portions which can be assembled, for example by gluing, riveting, heat welding, snap fitting, or interference fitting, for example. Parts can be produced by extrusion, grinding, molding, 3D printing, casting, or any other suitable method. A finish can be formed during production, or a coating or painted finish can be applied after production.

Accordingly, the disclosure provides a mounting base and holding system for table or wall mounting of an instrument of the disclosure. In use, holder 400A, including suction cup 430A, are pressed firmly downward against the surface 540) upon which holder 400A is to be mounted, by the user. In the process of this action the suction cup 430A is flattened at least partially and displaces air beneath it, until base 420 presses against a circular upper surface of suction base 420A. To increase suction, pin 454 is moved laterally, further raising a center of suction base 420A. Alternatively, substantially all suction is created by moving pin 454 laterally.

Figure 21:
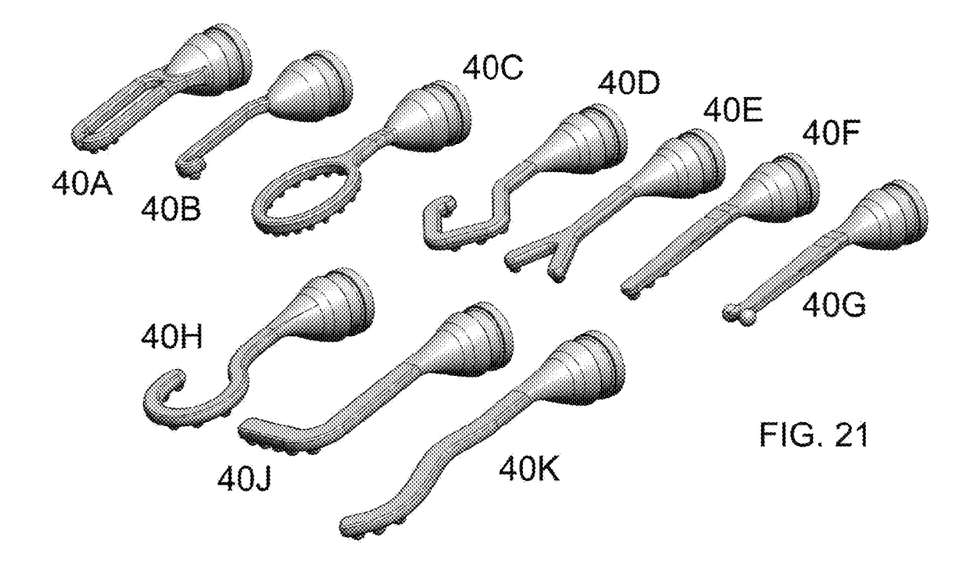
FIG. 21 depicts alternative tip shapes in accordance with the disclosure.

With reference to FIG. 21, alternative tip 40 shapes are presented, including elongate loop 40A, short hook 40B, ring 40C, open box 40D, fork 40E, single shaft 40F, single shaft with terminating bumps 40G, curved hook 40H, L-shape 40J, and open hook 40K. A medical practitioner can select a particular shape which best fits the anatomical treatment site, and which best transmits therapeutic vibration to the patient for the purposes stated herein. As with other embodiments of tip 40 described herein, the shaped tips 40A-40J can be bent to, for example, alter the desired shape to improve a fit, visibility, or to match a shape which has demonstrated improved results. For various tip shapes, it can be advantageous to orient body tissue at an angle with respect to a longitudinal axis of vibration of tip 40. For example, with reference to the tip of FIG. 12, a finger is placed orthogonal to a longitudinal axis of handle 12, a side portion of the finger thereby abutting both stop members 90. An injection, for example, can thereafter be made through the circular opening 92.

FIG. 22 depicts a kit 600 containing instrument 10, holder 400A, and components useful for a therapeutic treatment for diabetes. While kit 600 is targeted to diabetes, it should be understood that other kits can be formed which include instrument 10 and holder 400A, to be used for reducing pain in other therapeutic procedures. In the embodiment of FIG. 22, kit 600 includes a sealable case 602, a lancing device 604, lancets 606, instrument 10, holder 400A, a container of test strips 608, and a blood glucose analyzer 610, supported in a pouch 612.

All references cited herein are expressly incorporated by reference in their entirety. It will be appreciated by persons skilled in the art that the present disclosure is not limited to what has been particularly shown and described herein above. In addition, unless mention was made above to the contrary, it should be noted that all of the accompanying drawings are not to scale. There are many different features to the present disclosure and it is contemplated that these features may be used together or separately. Thus, the disclosure should not be limited to any particular combination of features or to a particular application of the disclosure. Further, it should be understood that variations and modifications of the subject matter of the disclosure might occur to those skilled in the art to which the disclosure pertains. Accordingly, all expedient modifications readily attainable by one versed in the art from the disclosure set forth herein that are in accordance with the disclosure are to be included as further embodiments of the present disclosure.

DRAWING REFERENCES

10 Instrument: 12 Handle: 24 Motor: 28 Electronic Circuit: 30A Vibration Transmitting Rod: 34 Nozzle: 40, 40A-H, 40J-K Tip: 50 Distal Tip Portion: 53 Lens: 60 Switch: 62 O-ring Support; 64 O-ring; 68 Rod Base Recess; 70 Output Shaft; 72 Rod Distal End; 74 Tip Recess; 76 Sleeve; 81 Arm; 100A Cam; 104 Cam Lobes; 280, 280A-D Nubs; 282 Arm Distal End; 286 Arm Front Face Portion; 288 Arm Rear Face Portion; 370 RFID Tag; 400 Mounting Base; 400A Holder; 404A Base Extension; 412 Instrument Holder; 414 Cradle Arm; 416 Cradle Arm; 420A Circular Base; 426A Planar Suction Base; 426B Peripheral Wall; 430A Suction Cup; 432A Yoke; 434A Cam Engagement; 436A Base Channel; 442A Handle or Holder Protrusion; 444A Handle or Holder Detent; 452 Yoke Aperture; 454 Cam Pin; 456 Base Apertures; 458 Cam Profile; 458' Cam Profile Deep Area; 458'' Cam Profile Shallow Area; 462 Cam Pin Buttons; 464 Resilient Bumper; 466 Bumper Upper End; 468 Bumper 10 Lower End; 540 Mounting Surface; 600 Kit; 602 Case; 604 Lancing Device; 606 Lancets; 608 Container of Test Strips; 610 Blood Glucose Analyzer; 612 Pouch.

What is claimed is:

1. A holder for mounting a hand tool to a surface, the holder comprising:
    a suction cup positionable upon the surface, the suction cup having a central area;
    a yoke connected to the central area, the yoke movable in a vertical direction relative to the surface, to distort the suction cup and create an area of low pressure between the suction cup and the surface, to secure the suction cup and yoke to the surface, the yoke including a cam engagement surface;
    a frame including
        a cradle shaped to receive and support the hand tool when the hand tool is placed onto the holder;
        a base;
        an extension connecting the base and the cradle; and
    a cam pin movable within the frame, the cam pin including a cam profile slideably engageable with the cam engagement surface of the yoke to push the yoke vertically away from the surface or allow the yoke to move towards the surface to increase or decrease the pressure between the suction cup and the surface,
wherein the yoke is biased by a resilient bumper.

2. The holder of claim 1, wherein the cradle includes at least two flexible legs.

3. The holder of claim 1, wherein the frame is fabricated from resilient plastic.

4. The holder of claim 1, wherein the cradle includes at least one of a projection or aperture, and wherein the hand tool includes the other of a mating aperture or projection, respectively, and wherein the projection and aperture mate when the hand tool is positioned within the cradle, to thereby maintain a predetermined position of the hand tool within the holder.

5. The holder of claim 1, wherein the pin moves along a plane parallel to the surface when the holder is mounted to the surface.

6. The holder of claim 1, wherein the pin passes through one or more apertures in the frame, and wherein an end of the pin forms an exposed button which can be pressed to move the pin.

7. The holder of claim 1, wherein the cam profile of the cam pin extends at a depth within the cam pin that varies along a longitudinal axis of the cam pin.

8. The holder of claim 7, wherein the cam profile faces away from the surface when the holder is positioned upon the surface.

9. The holder of claim 1, wherein the cam engagement surface faces toward the surface when the holder is positioned upon the surface.

10. The holder of claim 9, wherein the cam profile is oriented on a face of cam pin which faces away from the surface when the holder is positioned upon the surface, whereby the cam engagement surface is in operative engagement with the cam profile as the pin is moved.

11. The holder of claim 1, wherein the yoke is biased in a direction of the surface relative to the frame, when the holder is mounted upon the surface.

12. The holder of claim 1, wherein the bumper is affixed to the frame along a portion of its length, leaving a free portion in engagement with the yoke.

13. The holder of claim 12, wherein the cradle is connected to the frame at a non-orthogonal angle with respect to the surface when the holder is connected to the surface using the suction cup.

14. The holder of claim 1, wherein the yoke is co-molded to the suction cup.

15. The holder of claim 1, wherein the yoke is a different material than the suction cup.

16. A kit comprising a container sized and dimensioned to house and limit free movement of at least the holder of claim 1 and the hand tool.

17. The kit of claim 16, wherein the container is further sized and dimensioned to further house and limit free movement of a lancet driver tool, a plurality of lancets, a blood glucose reader, and a glucose test strip container.

* * * * *